(12) United States Patent
Lee et al.

(10) Patent No.: US 11,071,807 B2
(45) Date of Patent: Jul. 27, 2021

(54) LIQUID COMPOSITION INCLUDING ALGINIC ACID OR PHARMACEUTICALLY ACCEPTABLE SALT THEREOF AND COLLOIDAL POLYSACCHARIDE

(71) Applicant: MCNULTY PHARMA CO., LTD., Cheonan-si (KR)

(72) Inventors: Eun Jung Lee, Seoul (KR); Cheol Woo Lee, Suwon-si (KR)

(73) Assignee: MCNULTY PHARMA CO., LTD., Cheonan-si (KR)

( * ) Notice: Subject to any disclaimer, the term of this patent is extended or adjusted under 35 U.S.C. 154(b) by 0 days.

(21) Appl. No.: 16/619,333

(22) PCT Filed: Jun. 11, 2018

(86) PCT No.: PCT/KR2018/006617
§ 371 (c)(1),
(2) Date: Dec. 4, 2019

(87) PCT Pub. No.: WO2018/230915
PCT Pub. Date: Dec. 20, 2018

(65) Prior Publication Data
US 2020/0114047 A1  Apr. 16, 2020

(30) Foreign Application Priority Data
Jun. 12, 2017 (KR) .................. 10-2017-0073128

(51) Int. Cl.
*A61L 27/54* (2006.01)
*A61L 27/20* (2006.01)

(52) U.S. Cl.
CPC .............. *A61L 27/54* (2013.01); *A61L 27/20* (2013.01); *A61L 2400/06* (2013.01); *A61L 2430/34* (2013.01)

(58) Field of Classification Search
CPC ...... A61L 27/54; A61L 27/20; A61L 2400/06; A61L 2430/34
USPC ....................................................... 514/54
See application file for complete search history.

(56) References Cited

U.S. PATENT DOCUMENTS

| 2005/0208134 A1* | 9/2005 | Magdassi | ............. | A61K 9/0019 |
| | | | | 424/472 |
| 2010/0009932 A1* | 1/2010 | Boers | ...................... | A23L 33/40 |
| | | | | 514/54 |

FOREIGN PATENT DOCUMENTS

| JP | 2011-505377 A | 2/2011 |
| JP | 2016-540754 A | 12/2016 |
| JP | 2017-506208 A | 3/2017 |
| KR | 10-2014-0117270 A | 10/2014 |
| WO | 2005-039672 A1 | 5/2005 |
| WO | 2013-077357 A1 | 5/2013 |
| WO | 2015-009035 A1 | 1/2015 |
| WO | 2016-043547 A1 | 3/2016 |

OTHER PUBLICATIONS

Higuita-Castro et al. Soft Lithography-Based Fabrication of Biopolymer Microparticles for Nutrient Microencapsulation. Industrial Biotechnology, vol. 8 No. 6, p. 365-371, 2012. (Year: 2012).*

* cited by examiner

*Primary Examiner* — Yih-Horng Shiao
(74) *Attorney, Agent, or Firm* — Novick, Kim & Lee, PLLC; Jae Youn Kim

(57) ABSTRACT

A liquid composition includes: An alginic acid or a pharmaceutically acceptable salt thereof and a colloidal polysaccharide. The liquid composition of the present invention is suitable as a medical biomaterial for tissue repair to elevate mucosal tissues of the stomach and intestines during endoscopic resection. More specifically, the present invention relates to a submucosal injectable pharmaceutical liquid composition for use in endoscopic mucosal resection (EMR) or endoscopic submucosal dissection (ESD) for medical applications, including alginic acid having a weight average molecular weight of 100,000 to less than 200,000 or a pharmaceutically acceptable salt thereof and a colloidal polysaccharide. The liquid composition of the present invention is suitable for use as a preparation for submucosal local injection that can maintain mucosal elevation for a long time when injected during endoscopic mucosal resection or endoscopic submucosal dissection.

4 Claims, 3 Drawing Sheets

LIQUID COMPOSITION INCLUDING ALGINIC ACID OR PHARMACEUTICALLY ACCEPTABLE SALT THEREOF AND COLLOIDAL POLYSACCHARIDE

TECHNICAL FIELD

The present invention relates to a liquid composition including alginic acid or a pharmaceutically acceptable salt thereof and a colloidal polysaccharide that is suitable as a medical biomaterial for tissue repair to elevate mucosal tissues of the stomach and intestines during endoscopic resection.

BACKGROUND ART

The development of endoscopy and the extension of regular medical check-ups have led to a significant increase in the diagnosis rate of small adenomas and cancers. With the diversity of endoscopes and their accessories and the advances in endoscopic techniques, various endoscopic therapeutic procedures such as endoscopic mucosal resection (EMR), endoscopic submucosal dissection (ESD), endoscopic mucosal destruction, and endoscopic photodynamic therapy are utilized as local therapies for lesions that have traditionally relied on surgical operations.

Endoscopic mucosal resection (EMR) is a method for easily removing a mucosal lesion by topically injecting an appropriate solution into the submucosal layer, capturing the lesion with a snare, and conducting electricity to resect the lesion. EMR is typically used to remove lesions not bigger than 2 cm or remove lesions bigger than 2 cm little by little. The solution tends to disappear rapidly after injection. Flat and depressed lesions are difficult to find compared to elevated lesions. Large or difficult-to-access lesions are difficult to remove.

Since the late 1990's, the importance of en bloc resection and complete resection has been emphasized. Under such circumstances, endoscopic submucosal dissection (ESD) using an insulation-tipped electrosurgical knife (IT knife) has been developed and used for surgical treatment.

At the current moment where ESD is technically available, both conventional EMR and ESD are feasible for subcentimeter lesions. ESD is primarily considered for 1-2 cm lesions to which en bloc resection is difficult to apply and is in principle recommended for lesions bigger than 2 cm. Indeed, suitable surgical procedures should be determined considering the advantages of EMR (including simplicity and short operation time) and the disadvantages of ESD (including high incidence of complications and the need for advanced skill).

A mixture of physiological saline, epinephrine, and indigo carmine is the most frequently used submucosal injection solution. In some cases, highly viscous submucosal injection solutions (sodium hyaluronate or glycerol mixtures) with high osmotic pressure are used such that the submucosal layers remain elevated for a long time but they incur additional costs. Thus, there is a need to develop cheaper alternatives to existing submucosal injection solutions. Alginic acid salts are attracting attention as suitable alternatives.

In order to maintain a satisfactory level of mucosal elevation using a sodium alginate solution, however, the corresponding solution should not easily escape from the tissue. Thus, the sodium alginate is required to have a relatively high molecular weight. However, the high molecular weight sodium alginate is not relatively easily discharged through needles.

Particularly, when EMR or ESD is performed for the upper or lower gastrointestinal tract, 23G and 25G endoscopic puncture needles are used as standards for the injection of preparations for topical administration for the purpose of forming mucosal elevations. One of the characteristics required for submucosal injectable compositions is that the compositions should be able to easily pass through endoscopic puncture needles.

The following prior art documents are cited in this specification and are hereby incorporated by reference in their entirety.

PRIOR ART DOCUMENTS (Patent Document 1) PCT International Publication No. WO 2015-009035 (Jan. 22, 2015)
(Patent Document 2) PCT International Publication No. 2016-043547 (Mar. 24, 2016)
(Patent Document 3) PCT International Publication No. 2013-077357 (May 30, 2013)

DETAILED DESCRIPTION OF THE INVENTION

Problems to be Solved by the Invention

An object of the present invention is to provide a submucosal injectable composition that can replace expensive sodium hyaluronate, is effective in maintaining mucosal elevation for a long time, and can easily pass through an endoscopic puncture needle for EMR or ESD.

Means for Solving the Problems

The present invention has been made in an effort to solve the problems of the prior art and provides a submucosal injectable pharmaceutical liquid composition for use in endoscopic mucosal resection or endoscopic submucosal dissection for medical applications, including alginic acid having a weight average molecular weight of 100,000 to less than 200,000 or a pharmaceutically acceptable salt thereof and a colloidal polysaccharide.

In the present invention, the alginic acid or pharmaceutically acceptable salt thereof is present at a concentration of 0.05% (w/v) to 2.0% (w/v).

In the present invention, the colloidal polysaccharide includes a pectic substance or a pharmaceutically acceptable salt thereof.

In the present invention, the polysaccharide is present at a concentration of 0.01% (w/v) to 2.0% (w/v).

In the present invention, the alginic acid or pharmaceutically acceptable salt thereof and the pectic substance or pharmaceutically acceptable salt thereof are present in a ratio of 2:1 to 8:1 (w/v).

In the present invention, the composition has a pH of 5.0 to 8.0.

In the present invention, the composition has a viscosity of 1.0 to 50.0 centipoises (cps).

Effects of the Invention

The liquid composition of the present invention is suitable for use as a preparation for submucosal local injection that can maintain mucosal elevation for a long time when injected during endoscopic mucosal resection (EMR) or endoscopic submucosal dissection (ESD).

BEST MODE FOR CARRYING OUT THE INVENTION

Figure 1:
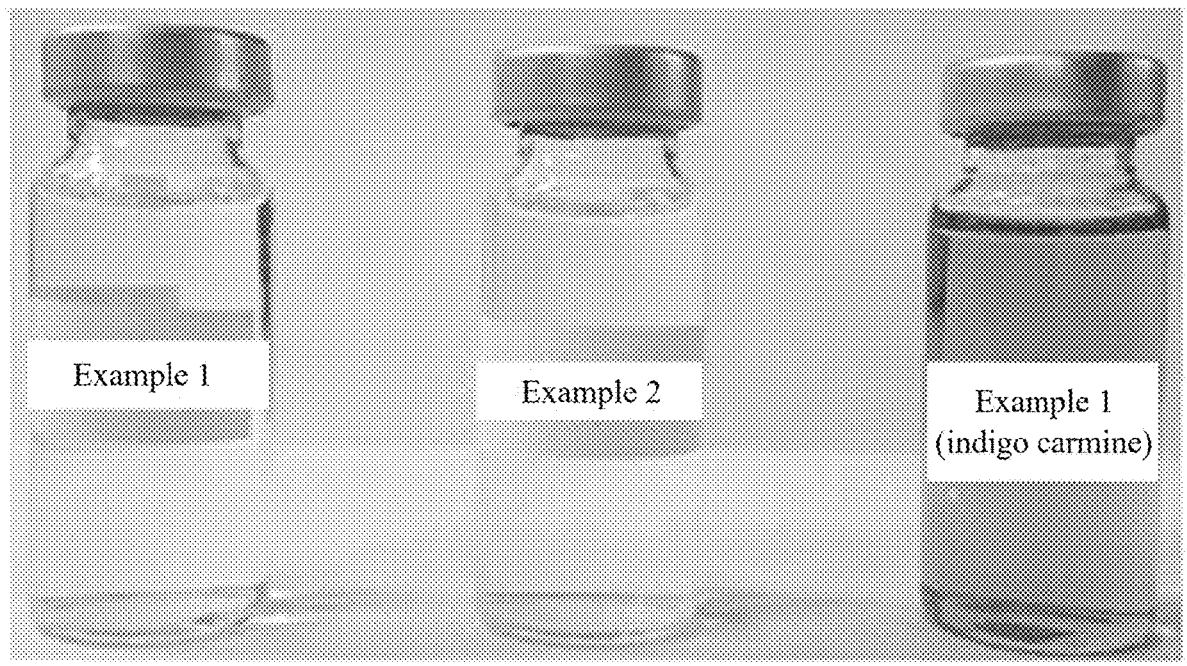
FIG. 1 shows a sample prepared in Example 1, a sample prepared in Example 2, and a sample prepared by adding indigo carmine dye to the sample prepared in Example 1 for visualization.

The present invention will now be described in detail.

The present invention provides a submucosal injectable pharmaceutical liquid composition for use in endoscopic mucosal resection or endoscopic submucosal dissection for medical applications, including alginic acid having a weight average molecular weight of 100,000 to less than 200,000 or a pharmaceutically acceptable salt thereof and a colloidal polysaccharide.

Alginic acid is a major constituent of the cell walls of brown algae. The alginic acid used in the composition of the present invention can be obtained by extraction from brown algae. Alginic acid has long been used in a variety of applications due to its unique physical properties, including the ability to form gels, high viscosity, and the ability to form films.

For example, alginic acid has been used as a stabilizer, viscosifier or gelling agent in various industrial fields, including food, printing, and pharmaceutical industries. Alginic acid has also been used as a raw material for drug delivery systems such as microspheres, beads, microcapsules or tablets and as a matrix carrier in tissue engineering.

The alginic acid used in the composition of the present invention has a weight average molecular weight of 100,000 to less than 200,000. Higher molecular weight alginic acid has a better ability to maintain mucosal elevation than lower molecular weight alginic acid but tends to have difficulty in passing through endoscopic puncture needles, making it difficult to apply to endoscopic procedures. In view of this, it is preferred that the alginic acid used in the composition of the present invention has a weight average molecular weight of less than 200,000 for better flowability of the composition in the form of an injectable solution and better discharge of the composition from puncture needles. The ability of the weight alginic acid having a weight average molecular weight of less than 200,000 to maintain mucosal elevation is inferior to that of higher molecular weight alginic acid, but this problem is solved by the addition of the colloidal polysaccharide (particularly a pectic substance), which will be described below.

The alginic acid is not particularly limited as long as it is suitable for medical applications and has a weight average molecular weight of 100,000 to less than 200,000. The pharmaceutically acceptable salt of alginic acid is not particularly limited and examples thereof include pharmaceutically acceptable alkali metal salts of alginic acid (sodium and potassium salts, etc.), pharmaceutically acceptable alkaline earth metal salts of alginic acid (calcium and magnesium salts, etc.), pharmaceutically acceptable salts of alginic acid with inorganic bases (ammonium salts, etc.), and pharmaceutically acceptable salts of alginic acid with organic bases (propylene glycolate, etc.). Among these salts, alkali metal salts of alginic acid are preferred and sodium alginate is particularly preferred.

Sodium alginate is a naturally derived biomaterial that is in the form of a white to pale yellow fibrous grain, granule or powder and is almost odorless and tasteless. Sodium alginate is used to increase the stickiness and viscosity of food, to enhance the emulsion stability of food, and improve the physical properties and tactility of food. For example, sodium alginate is used as an ice cream stabilizer, a ketchup, mayonnaise or sauce tackifier, a refined rice wine clarifier, a gelling agent, an emulsifier or a thickener. Sodium alginate is a polymer material that is available in various grades of purity. Sodium alginate becomes viscous when dissolved in water and a 1% aqueous sodium alginate solution is almost neutral (pH 6-8) (NF 24 page, 2008). Sodium alginate is hardened with NaCl or at low pH. This feature explains the use of sodium alginate is used as a thickener, etc. Sodium alginate has a structure represented by Formula 1:

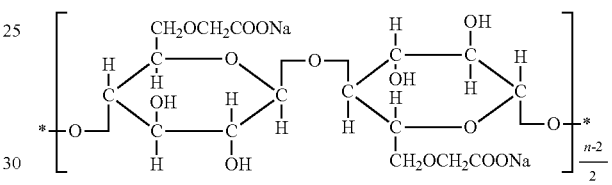

[Formula 1]

The concentration of the alginic acid or pharmaceutically acceptable salt thereof in the composition of the present invention can be properly selected. As the concentration of the alginic acid or pharmaceutically acceptable salt thereof increases, the viscosity of the composition increases, making it difficult for the composition to pass through an endoscopic puncture needle. Accordingly, it is preferred that the concentration of the alginic acid or pharmaceutically acceptable salt thereof and the viscosity of the composition are low. Meanwhile, if the concentration of the alginic acid or pharmaceutically acceptable salt thereof is excessively low, the ability of the composition to elevate the mucosa does not reach a desired level.

The concentration of the alginic acid or pharmaceutically acceptable salt thereof in the composition of the present invention is preferably 0.05% (w/v) to 2.0% (w/v), more preferably 0.05% (w/v) to less than 1.5% (w/v), even more preferably 0.05% (w/v) to 1.0% (w/v).

The term "polysaccharide" as used herein refers collectively to a long chain of monosaccharides linked by glycosidic bonds. Such polysaccharides include alginate, pectic substances, guar gum, dextran, xanthan gum, chitosan, chondroitin, hyaluronic acid, heparin, amylose, amylopectin, glycogen, cellulose, chitin, keratan sulfate, and peptidoglycan. The polysaccharide includes alginic acid in a broad sense but is defined to exclude alginic acid and hyaluronic acid.

The concentration of the polysaccharide in the composition of the present invention is preferably 0.01% (w/v) to 2.0% (w/v), more preferably 0.01% (w/v) to less than 1.0% (w/v), even more preferably 0.01% (w/v) to 0.5% (w/v).

The polysaccharide is preferably a pectic substance or a pharmaceutically acceptable salt thereof. The pharmaceutically acceptable salt of the pectic substance is not particularly limited and examples thereof include pharmaceutically acceptable alkali metal salts of the pectic substance (sodium and potassium salts, etc.) and pharmaceutically acceptable alkaline earth metal salts of the pectic substance (calcium and magnesium salts, etc.).

Examples of such pectic substances include protopectin, pectin, pectic acid, and pectinic acid, which are chemically different polysaccharides based on polymeric acidic polysaccharides obtained by polycondensation of D-galacturonic acid into normal chain forms and are interconvertible. These pectic substances are linked to each other via phosphate bonds or arabinose or galactose-mediated bonds to be helpful in maintaining the shape of the cell membrane. Accordingly, pectic substances possess all characteristics of these chemically different polysaccharides. Particularly, pectic substances are applied to jam and jelly making because they are likely to gel In addition, pectic substances are widely used not only as emulsifiers for foods and coating agents for dried snacks but also in cosmetics, tooth powders, gelling agents, and pharmaceutical drugs (intestinal drugs) based on their emulsifying properties. Protopectin is abundantly found in immature fruits. As fruits mature, protopectin is sequentially degraded to pectinic acid, pectic acid, and finally to low molecular weight polygalacturonic acid, which determines the firmness of the fruits.

Pectin is thought to be a linear molecule composed of α-1,4 linked D-galacturonic acid and its structure is represented by Formula 2:

[Formula 2]

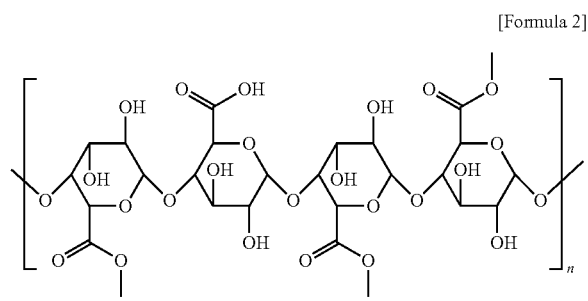

Some of the carboxyl groups of the galacturonic acid are methyl esterified and some of them are neutralized with a base to form mainly the middle lamella of cell walls.

Since plant-derived pectin is likely to denature during extraction from plant, storage, and processing, its structure is difficult to define. Pectin has a molecular weight between 50,000 and 150,000 daltons.

Pectin is classified according to the degree of esterification.

A relatively high proportion of the carboxyl groups in high (methyl) ester (HM) pectin are methyl esterified and the remaining carboxylic acid groups exist in the form of free acids or as ammonium, potassium, calcium or sodium salts. The characteristics of HM-pectin may vary depending on the degrees of esterification and polymerization. Pectin in which less than 50% of the carboxyl acid units exist as methyl esters are normally referred to as low (methyl) ester (LM) pectin. The treatment of high ester pectin under weakly acidic or alkaline conditions yields low ester pectin.

Alkaline de-esterification of amidated pectin using ammonia produces high ester pectin. In this type of pectin, some of the remaining carboxylic acid groups are transformed into the acid amide. The properties of amidated pectin may vary with the proportion of ester and amide units and with the degree of polymerization. Commercially available pectin is usually mixed with sugar for the purpose of standardization and a certain type thereof contains a buffer salt for pH adjustment or desired characteristics.

In the composition of the present invention, the alginic acid or pharmaceutically acceptable salt thereof and the pectic substance or pharmaceutically acceptable salt thereof may be present in a ratio of 2-8:1 (w/v). If the proportion of the pectic substance is less than the lower limit defined above, the effect of maintaining mucosal elevation may be negligible. Meanwhile, if the proportion of the pectic substance exceeds the upper limit defined above, there is a risk that the composition may not pass through a puncture needle. This will be understood by the following examples, including experimental example.

The composition of the present invention may include a pharmaceutically acceptable solvent. The solvent is not particularly limited and examples thereof include water (preferably water for injection) and physiological saline. The composition of the present invention may further include a phosphate buffer solution for pH adjustment, preferably to a pH 5.0 to 8.0.

The composition of the present invention may include one or more pharmaceutically active ingredients or one or more general pharmaceutical ingredients selected from the group consisting of stabilizers, emulsifiers, buffers, isotonic agents, preservatives, analgesics, colorants, binders, lubricants, suspending agents, antioxidants, pH adjusting agents, dispersants, solubilizers, solubilizing agents, and dissolution aids as long as the effects of the invention are not impaired.

The composition of the present invention may include a pharmaceutically acceptable dye, for example, a dye for better visualization, such as indigo carmine. The injection of the colored composition into the submucosa makes the injected area of the submucosa visible well. In addition, the dye can easily and reliably visualize the composition injected into the submucosal layer. Accordingly, the use of the dye contributes to improvements in the operational effectiveness and stability of EMR or ESD.

The composition of the present invention is injected into the submucosal layer for EMR or ESD. The mucosa is not particularly limited. As the mucosa, there may be mentioned, for example, the digestive mucosa (for example, the oral mucosa or the gastrointestinal mucosa), respiratory mucosa (for example, nasal septum mucosa) or the urogenital mucosa (for example, the bladder mucosa, the vaginal mucosa or the uterine mucosa). The digestive mucosa is preferred.

The gastrointestinal mucosa is particularly preferred. The gastrointestinal mucosa may be, for example, the esophageal mucosa, the gastric mucosa, the duodenal mucosa or the colonic mucosa.

The composition of the present invention is applied to endoscopic mucosal resection (EMR) or endoscopic submucosal dissection (ESD). For a surgical procedure, the composition is injected into the submucosal layer of a site where epithelial elevation is needed. When the composition of the present invention is injected into the submucosal layer, the alginic acid or pharmaceutically acceptable salt thereof is retained at the injection site to elevate the mucosa. A syringe is preferably used to inject the composition of the present invention to prevent leakage of the composition or administration of the composition to a desired site. Since the injected composition elevates the mucosa around a lesion, medical treatment for the lesion is easy to perform, enabling more rapid and reliable removal of the lesion.

The dose of the composition according to the present invention is not limited and can be properly determined depending on the size or site of the lesion. For example, the composition of the present invention is generally injected in an amount of about 5 to about 60 mL when applied to human EMR or ESD.

The composition of the present invention may be provided as a package of injectable preparations in syringes in which a part or all of the constituents of the composition are filled. In this case, the injectable preparations may be diluted and mixed just prior to use. An endoscopic injection needle can be simply fitted onto the tip of each syringe to immediately inject the composition of the present invention during a surgical procedure. In the case where the stability of the alginic acid or pharmaceutically acceptable salt thereof is impaired by the other ingredients, the alginic acid or pharmaceutically acceptable salt thereof may be formulated into a preparation that is mixed in situ with the corresponding ingredients just before a surgical procedure.

The liquid composition for endoscopic use according to the present invention is preferably used to resect mucosal tissues of the stomach and intestines. That is, when it is intended to resect a polyp or cancer, the liquid composition of the present invention is injected into the submucosal layer through an endoscopic puncture needle to elevate the polyp or cancer and the elevated site is resected with a snare (a wire with a loop) or a needle knife.

MODE FOR CARRYING OUT THE INVENTION

The present invention will be more specifically explained with reference to the following examples. However, it should be noted that these examples are provided for illustrative purposes only and are not intended to limit the scope of the present invention.

EXAMPLE 1

Sodium alginate (weight average molecular weight: ~130,000-150,000) was dissolved in water to prepare a 0.08% (w/v) aqueous solution. 0.02% (w/v) pectin was added to the aqueous solution, and then an isotonic agent, a buffer or a pH adjusting agent and a stabilizer were added thereto. The aqueous solution had a pH of 7.0±0.5, an osmotic pressure of 285.0±15.0 mOsm, and a viscosity of 2.5±0.5 cps. The mixture was stirred for complete dissolution. The composition was passed through a 0.2 μm filter, placed in a vial sealed with a rubber cap and an aluminum crimp, and sterilized at 121° C. for 20 min.

EXAMPLE 2

Sodium alginate (weight average molecular weight: ~130,000-150,000) was dissolved in water to prepare a 0.06% (w/v) aqueous solution. 0.015% (w/v) pectin was added to the aqueous solution, and then an isotonic agent, a buffer or a pH adjusting agent and a stabilizer were added thereto. The aqueous solution had a pH of 7.0±0.5, an osmotic pressure of 280.0±10.0 mOsm, and a viscosity of 2.5±0.5 cps. The mixture was stirred for complete dissolution. The composition was passed through a 0.2 μm filter, placed in a vial sealed with a rubber cap and an aluminum crimp, and sterilized at 121° C. for 20 min.

FIG. 1 shows the sample prepared in Example 1 and the sample prepared in Example 2. Indigo carmine dye was added to the sample prepared in Example 1 for visualization. This sample is also shown in FIG. 1.

COMPARATIVE EXAMPLE 1

A 0.4% (w/v) sodium hyaluronate solution was used.

COMPARATIVE EXAMPLE 2

Physiological saline (Normal Saline, NS) was used.

EXPERIMENTAL EXAMPLE 1

Evaluation of Ability to Elevate the Mucosa

Figure 2:
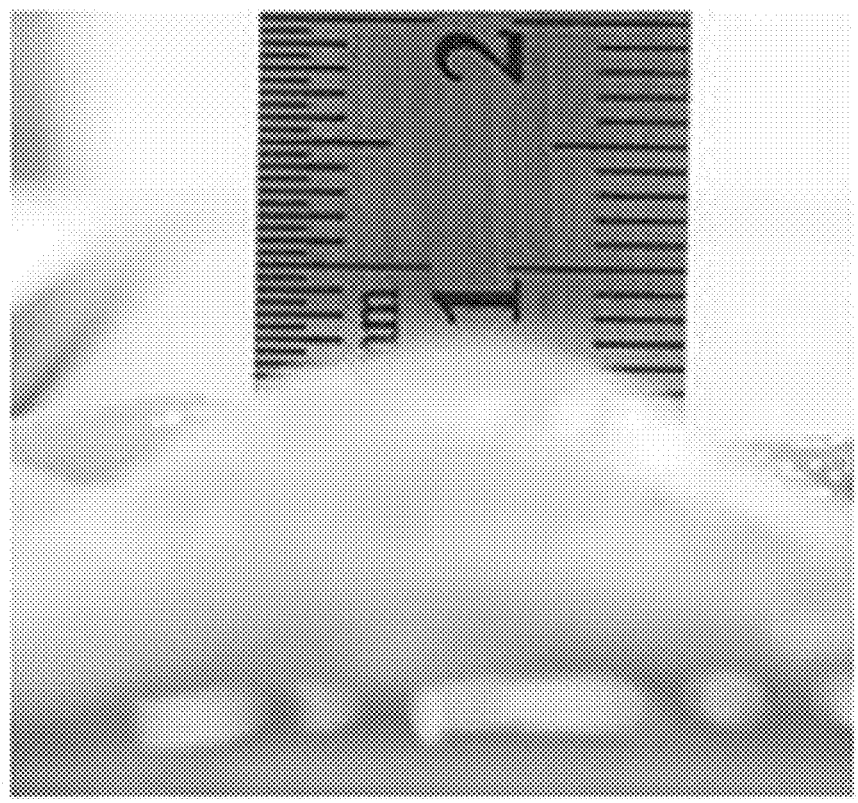
FIG. 2 shows the heights of mucosal elevations of an excised porcine stomach after injection of samples of Comparative Examples 1 and 2 and samples prepared in Examples 1 and 2, which were observed with naked eyes.
Figure 3:
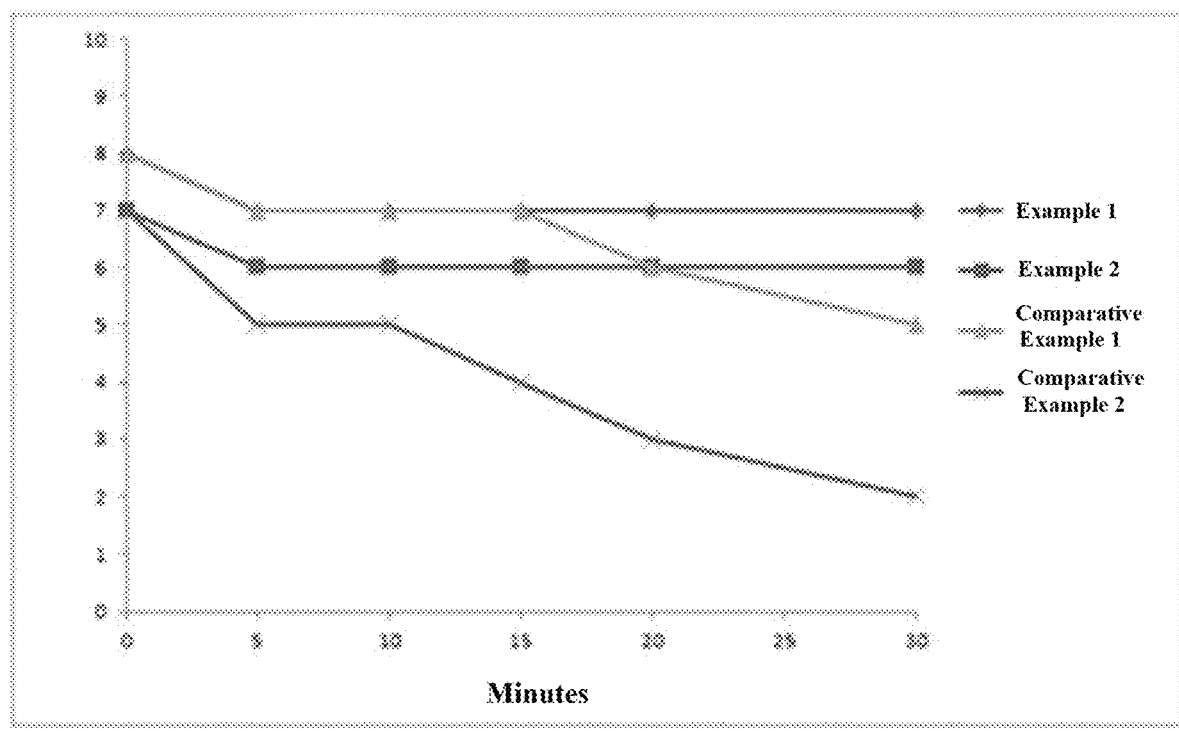
FIG. 3 shows the heights of mucosal elevations of an excised porcine stomach for 30 minutes after injection of samples of Comparative Examples 1 and 2 and samples prepared in Examples 1 and 2.

The heights of mucosal elevations of an excised porcine stomach after injection of the samples of Comparative Examples 1 and 2 and the samples prepared in Examples 1 and 2 were observed with naked eyes. The heights of mucosal elevations immediately, 5 min, 10 min, 15 min, 20 min, and 30 min after submucosal injection were observed with naked eyes, as shown in FIG. 2. Each measurement was done in triplicate and averaged. The results are shown in Table 1 and FIG. 3.

TABLE 1

| | Tim (min) | | | | | |
|---|---|---|---|---|---|---|
| Height (mm) | Immediately after injection | 5 min after injection | 10 min after injection | 15 min after injection | 20 min after injection | 30 min after injection |
| Example 1 | 8 | 7 | 7 | 7 | 7 | 7 |
| Example 2 | 7 | 6 | 6 | 6 | 6 | 6 |
| Comparative Example 1 | 8 | 7 | 7 | 7 | 6 | 5 |
| Comparative Example 2 | 7 | 5 | 5 | 4 | 3 | 2 |

Even 30 min after injection, the mucosa remained elevated.

Evaluation of Ease of Passage Through Endoscopic Puncture Needles 10 mL of each of the samples was filled in a 10 mL injection vessel (jig) equipped with an endoscopic puncture needle (needle diameter 23G), and a piston of the injection vessel was pushed at a constant rate of 0.2 mm/sec to discharge the sample from the tip of the endoscopic puncture needle. The force (Kgf) required to discharge the sample was measured. The measurement was done in triplicate (compact table-top universal tester: KANA, IM-010). The measured values were averaged. The results are shown Table 2.

TABLE 2

| | Discharge pressure (Kgf) |
|---|---|
| Example 1 | 0.31 |
| Example 2 | 0.36 |
| Comparative Example 1 | 2.54 |
| Comparative Example 2 | 0.30 |

The inventive compositions maintained the mucosal elevations even 30 minutes after injection and their discharge pressures were lower than the sodium hyaluronate solution and were comparable to the physiological saline, demonstrating their practicality. These results lead to the conclusion that the inventive compositions are suitable for use in EMR or ESD.

The invention claimed is:

1. A submucosal injectable pharmaceutical liquid composition suitable for use in endoscopic mucosal resection or endoscopic submucosal dissection in medical applications, comprising an alginic acid sodium salt having a weight average molecular weight of 100,000 to 150,000 and a colloidal polysaccharide that comprises a pectic substance or a pharmaceutically acceptable salt thereof, wherein the composition has a pH of 5.0 to 8.0, and the alginic acid sodium salt and the pectic substance or the pharmaceutically acceptable salt thereof are present in a ratio of 2:1 to 8:1 by concentration (w/v) and wherein the suitability for use is determined by maintaining mucosal elevation with a consistent height even 30 min after submucosal injection.

2. The liquid composition according to claim 1, wherein the alginic acid sodium salt is present at a concentration of 0.05% (w/v) to 2.0% (w/v).

3. The liquid composition according to claim 1, wherein the colloidal polysaccharide is present at a concentration of 0.01% (w/v) to 2.0% (w/v).

4. The liquid composition according to claim 1, wherein the composition has a viscosity of 1.0 to 50.0 centipoises (cps).

* * * * *